(12) United States Patent
Asami

(10) Patent No.: US 11,627,931 B2
(45) Date of Patent: Apr. 18, 2023

(54) ULTRASONIC IMAGING DEVICE AND METHOD

(71) Applicant: Hitachi, Ltd., Tokyo (JP)

(72) Inventor: Rei Asami, Tokyo (JP)

(73) Assignee: FUJIFILM HEALTHCARE CORPORATION, Chiba (JP)

(*) Notice: Subject to any disclaimer, the term of this patent is extended or adjusted under 35 U.S.C. 154(b) by 602 days.

(21) Appl. No.: 16/647,164

(22) PCT Filed: Oct. 16, 2018

(86) PCT No.: PCT/JP2018/038481
§ 371 (c)(1),
(2) Date: Mar. 13, 2020

(87) PCT Pub. No.: WO2019/171647
PCT Pub. Date: Sep. 12, 2019

(65) Prior Publication Data
US 2020/0229787 A1    Jul. 23, 2020

(30) Foreign Application Priority Data
Mar. 7, 2018 (JP) .............................. JP2018-040908

(51) Int. Cl.
A61B 8/06 (2006.01)
A61B 8/14 (2006.01)
(Continued)

(52) U.S. Cl.
CPC .............. *A61B 8/06* (2013.01); *A61B 8/14* (2013.01); *A61B 8/461* (2013.01); *A61B 8/488* (2013.01); *A61B 8/5223* (2013.01)

(58) Field of Classification Search
CPC .. A61B 8/06; A61B 8/14; A61B 8/461; A61B 8/488; A61B 8/5223
See application file for complete search history.

(56) References Cited

U.S. PATENT DOCUMENTS

2003/0023165 A1* 1/2003 Okabayashi ............. A61B 8/06
                                                                            600/443
2005/0004462 A1* 1/2005 Sakaguchi ............... A61B 8/06
                                                                            600/441
(Continued)

FOREIGN PATENT DOCUMENTS

CN        102266239 A      12/2011
CN        106028948 A      10/2016
(Continued)

OTHER PUBLICATIONS

Daniel Posada, et al., "Staggered Multiple-PRF Ultrafast Color Doppler", IEEE Transactions on Medical imaging, vol. 35, No. 6, Jun. 2016, pp. 1510-1521.
(Continued)

*Primary Examiner* — Bo Joseph Peng
(74) *Attorney, Agent, or Firm* — Mattingly & Malur, PC

(57) ABSTRACT

Provided is a technique capable of preventing a deterioration of a frame rate or a temporal resolution and estimating a blood flow velocity in a wide velocity range. A method is based on an unequal interval transmission method, and calculates a blood flow velocity by using a temporally adjacent received signal set and a temporally discontinuous received signal set, among a plurality of received signals obtained via a plurality of times of transmission in one transmission direction. When a number of the adjacent received signal set and a number of the temporally discontinuous received signal set are the same, an expansion of the velocity range similar to an unequal interval transmission in related art can be realized and the frame rate can be improved.

9 Claims, 12 Drawing Sheets

(51) Int. Cl.
    *A61B 8/00*        (2006.01)
    *A61B 8/08*        (2006.01)

(56)            References Cited

U.S. PATENT DOCUMENTS

2005/0148875  A1      7/2005   Sato
2014/0005537  A1*     1/2014   Asami ................. A61K 49/225
                                                              600/407
2015/0366540  A1     12/2015   Sato

FOREIGN PATENT DOCUMENTS

JP          04-279864  A      10/1992
JP         2005-176997 A       7/2005
JP         2005-312632 A      11/2005
JP         2016-002379 A       1/2016

OTHER PUBLICATIONS

International Search Report of PCT/JP2018/038481 dated Dec. 25, 2018.
International Preliminary Report on Patenteability received in corresponding International Application No. PCT/JP2018/038481 dated Sep. 8, 2020.
Chinese Office Action received in corresponding Chinese Application No. 2018800568321.1 dated Mar. 28, 2022.
Chinese Office Action received in corresponding Chinese Application No. 201880056832.1 dated Oct. 19, 2022.

* cited by examiner

[FIG. 1]
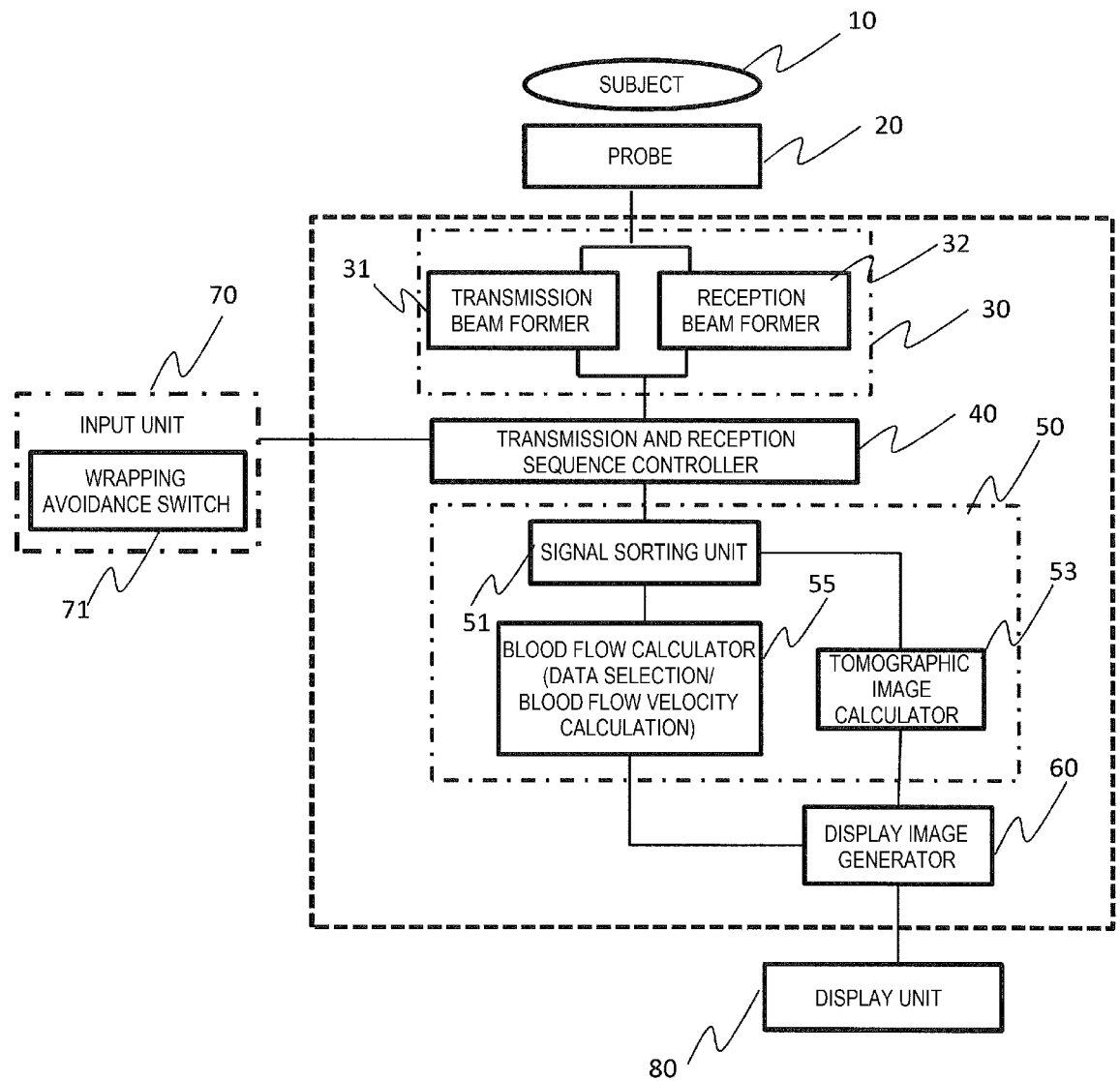

[FIG. 2A]
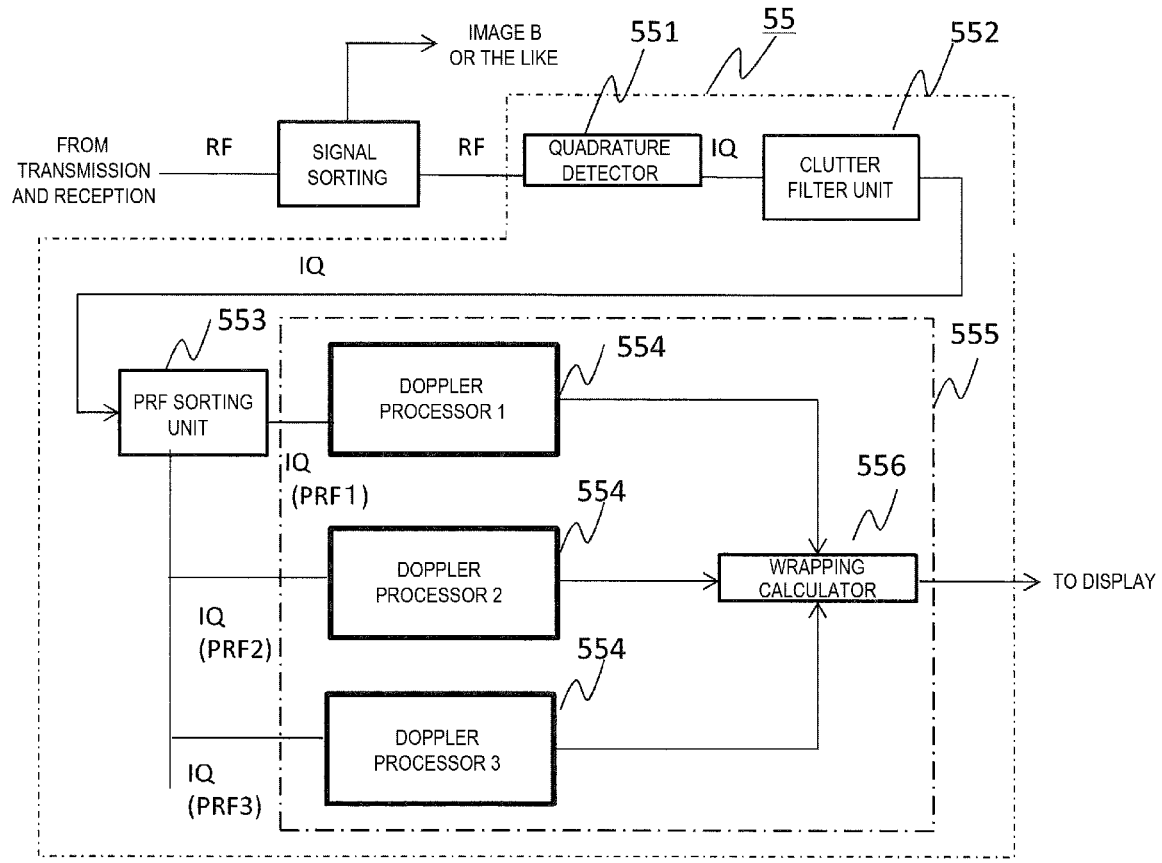
[FIG. 2B]
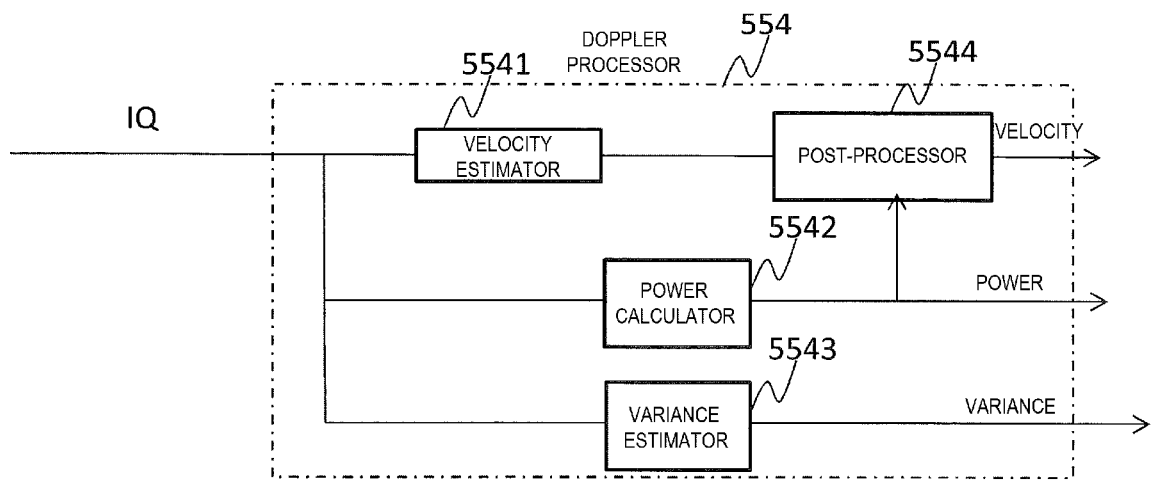

[FIG. 3]
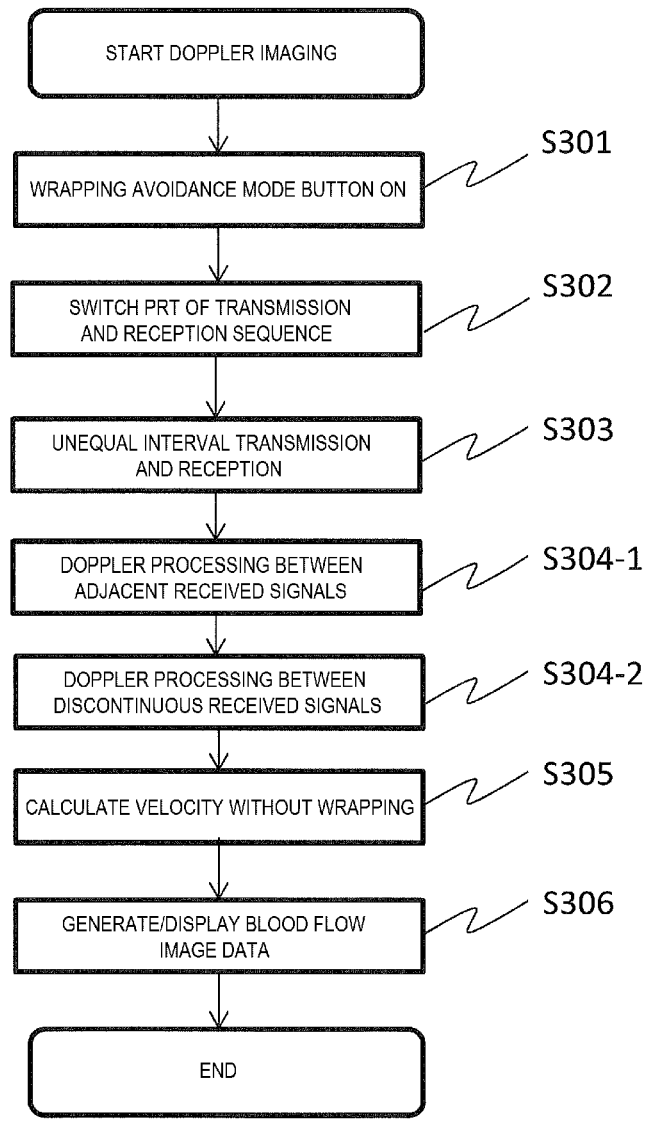

[FIG. 4]
(a)
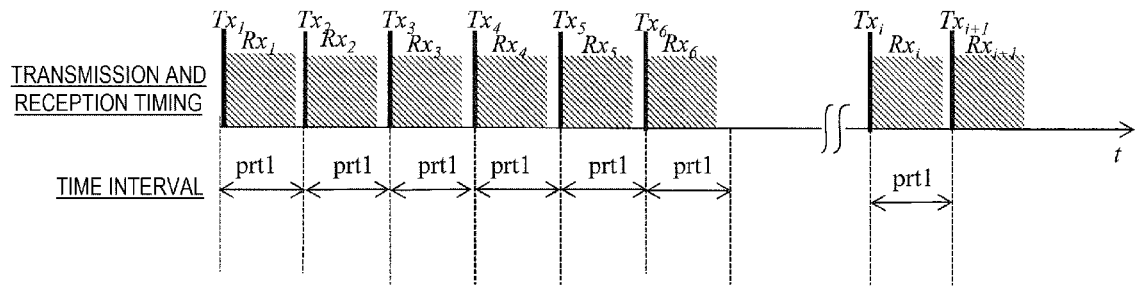
(b)
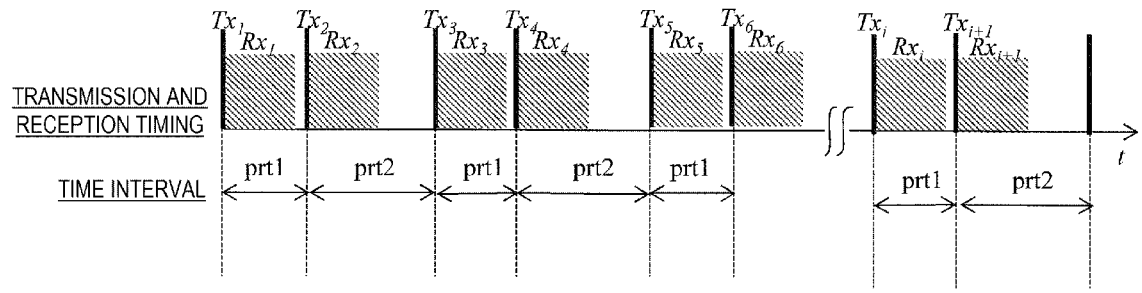
[FIG. 5]
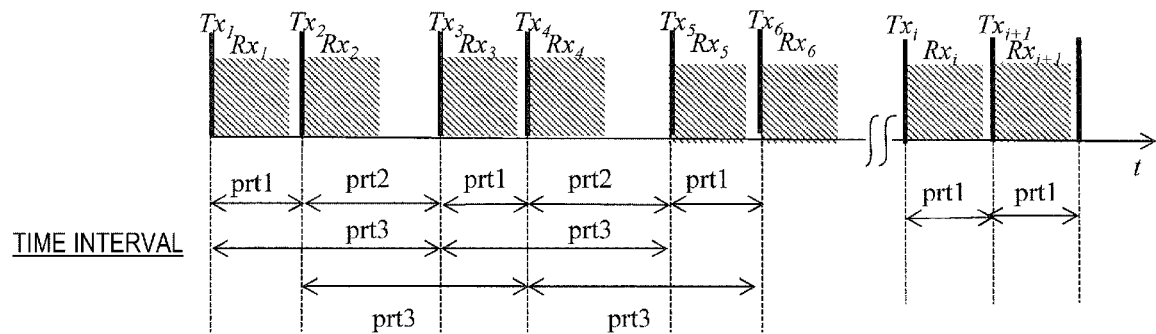

[FIG. 6]
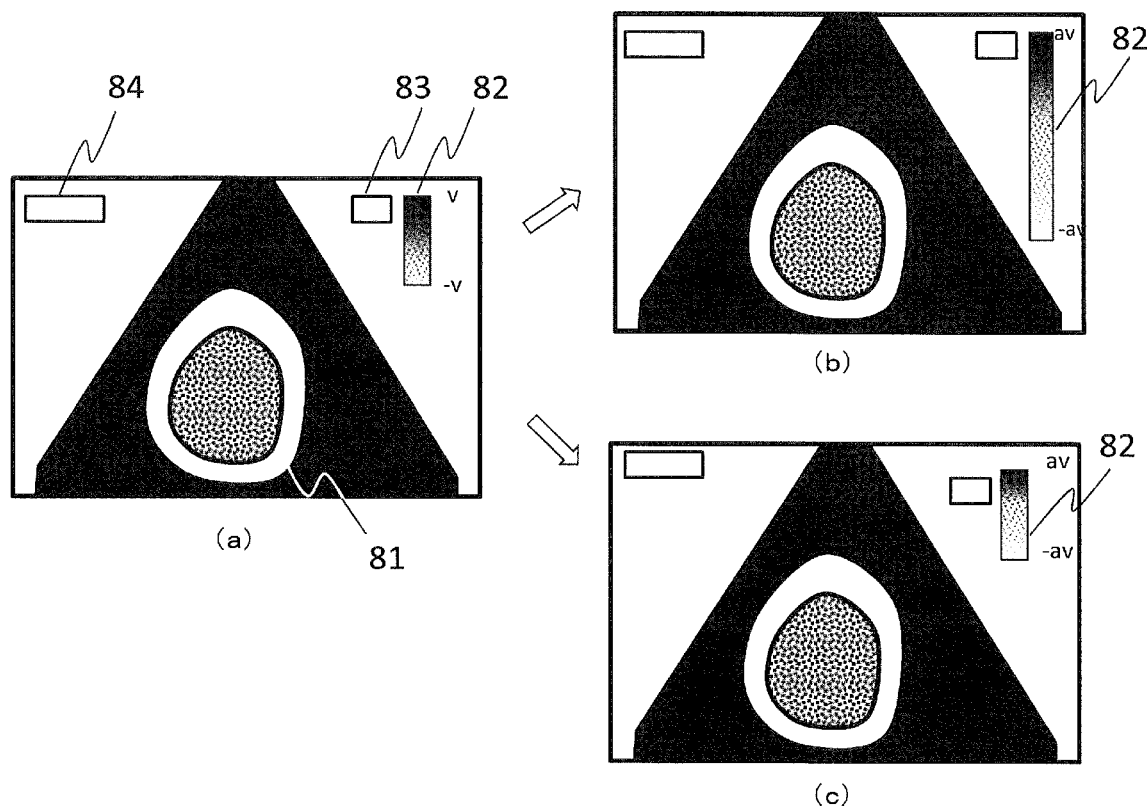

[FIG. 7]

| | SEQUENCE | TIME FOR ACQUIRING ONE SCANNING LINE | VELOCITY RANGE | FR |
|---|---|---|---|---|
| DOPPLER IN RELATED ART | | $prt_1*9$ | 1 | 1 |
| UNEQUAL INTERVAL TRANSMISSION METHOD | | $prt_1*9+prt_2*8= prt_1*19.7$ | 3 | 0.4 |
| METHOD ACCORDING TO EMBODIMENT | | $prt_1*8+prt_2*4= prt_1*13.3$ | 3 | 0.7 |

$prt_1$
$prt_2$
$prt_3$

[FIG. 8]
(a)
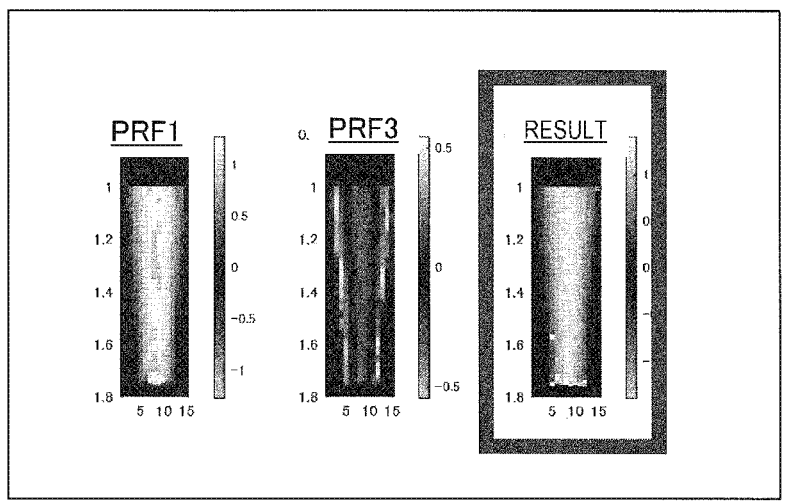
(b)
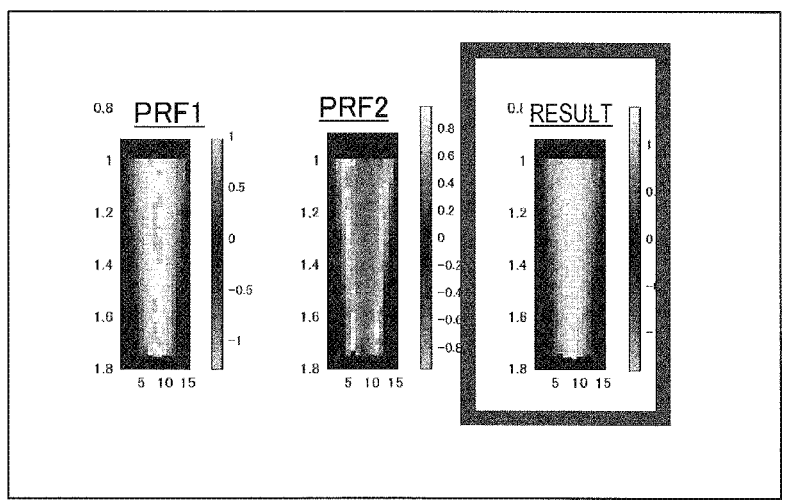

[FIG. 9]
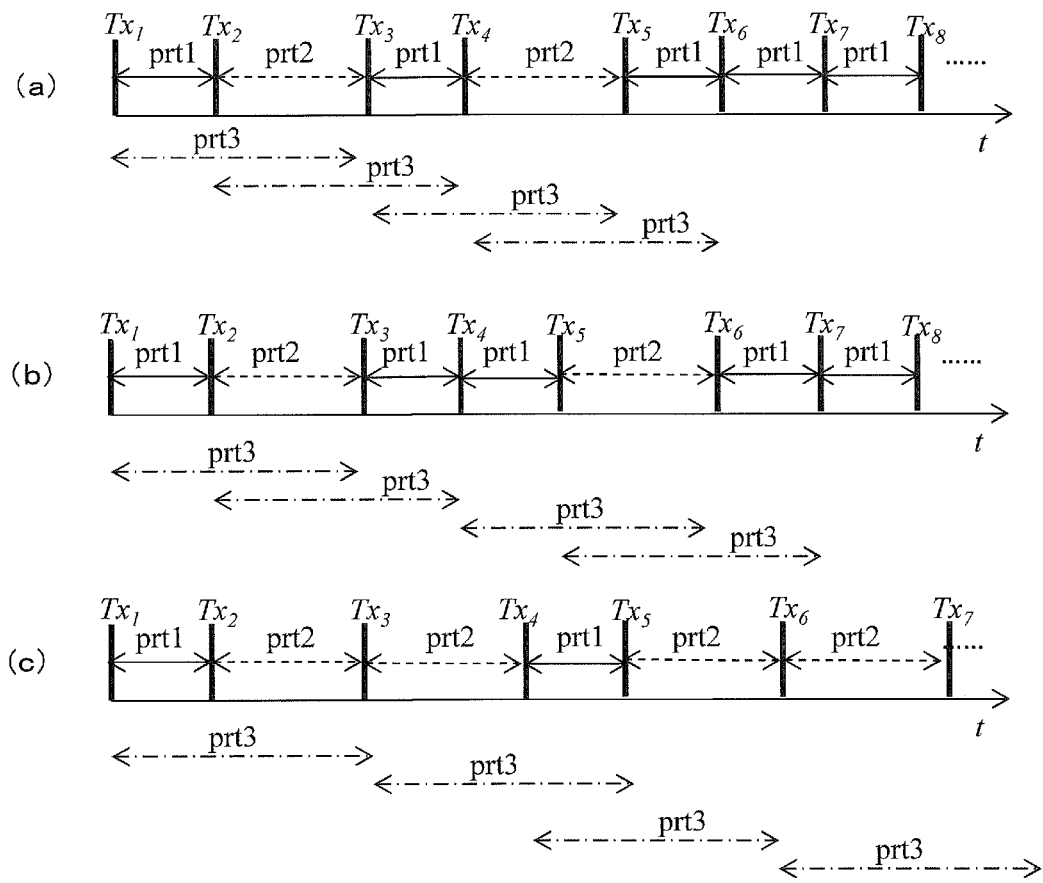

[FIG. 10]
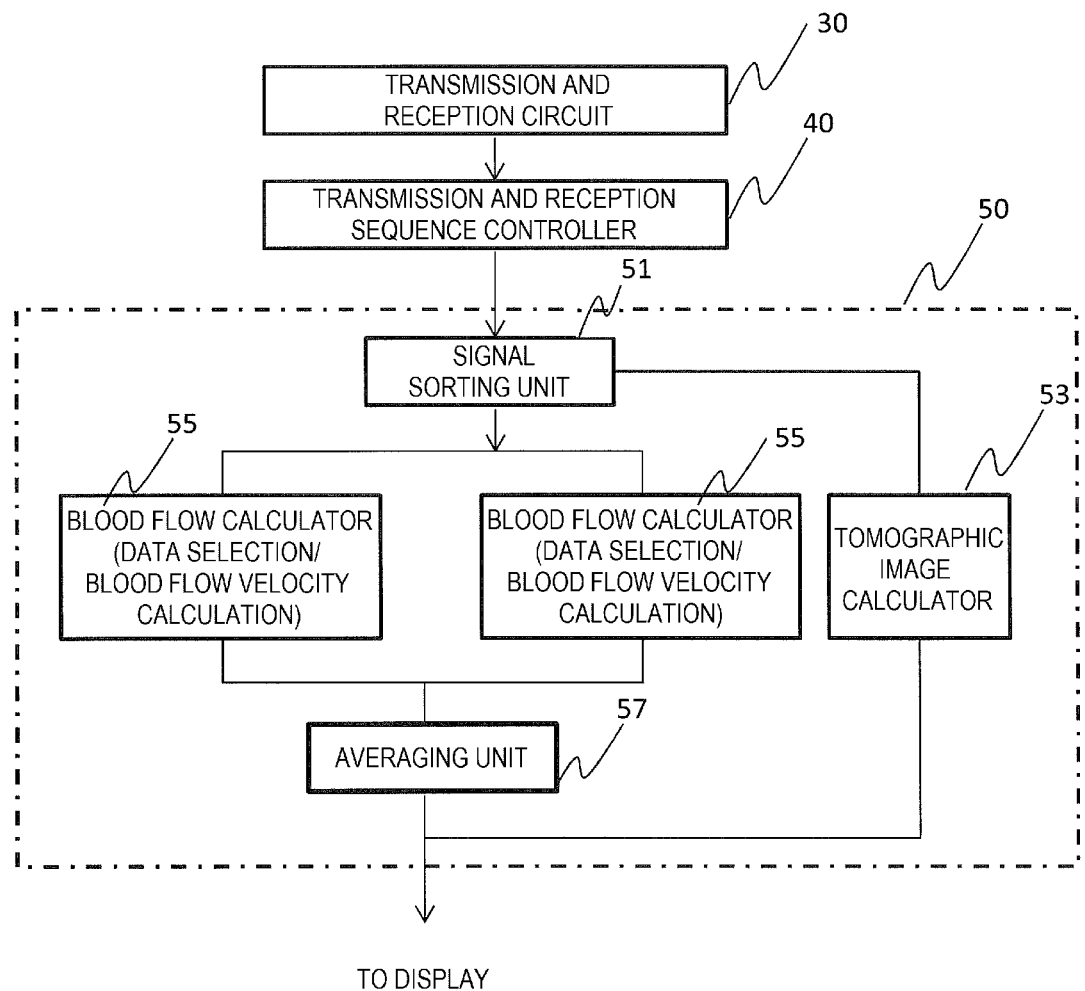

[FIG. 11]
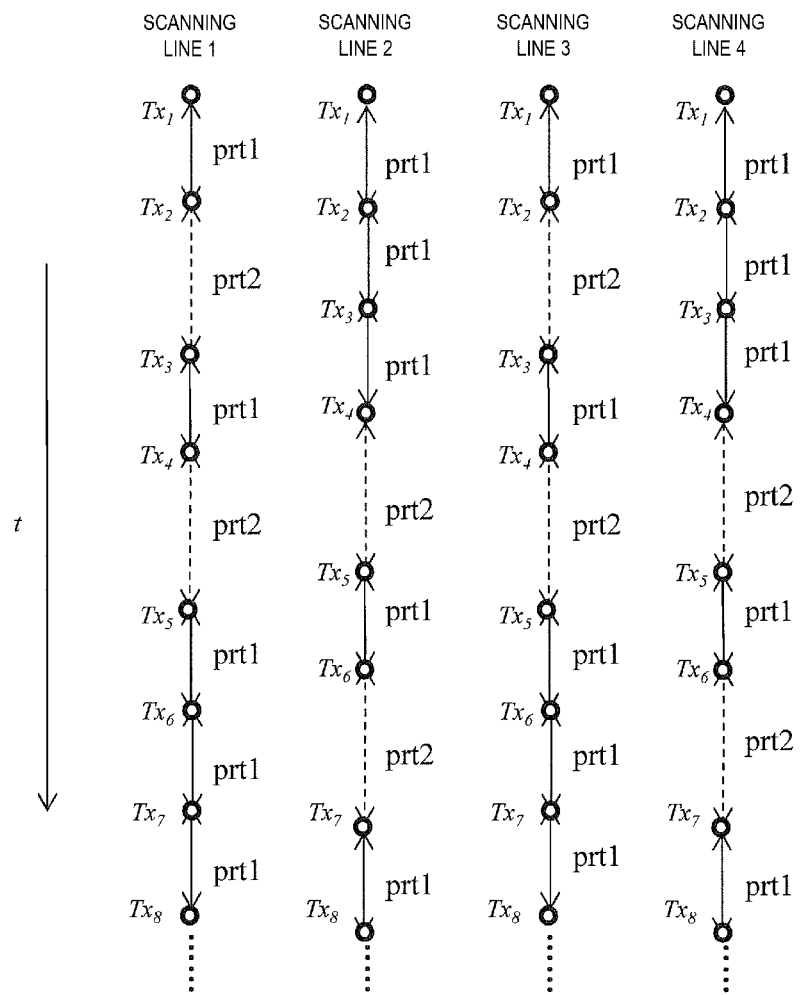

[FIG. 12]
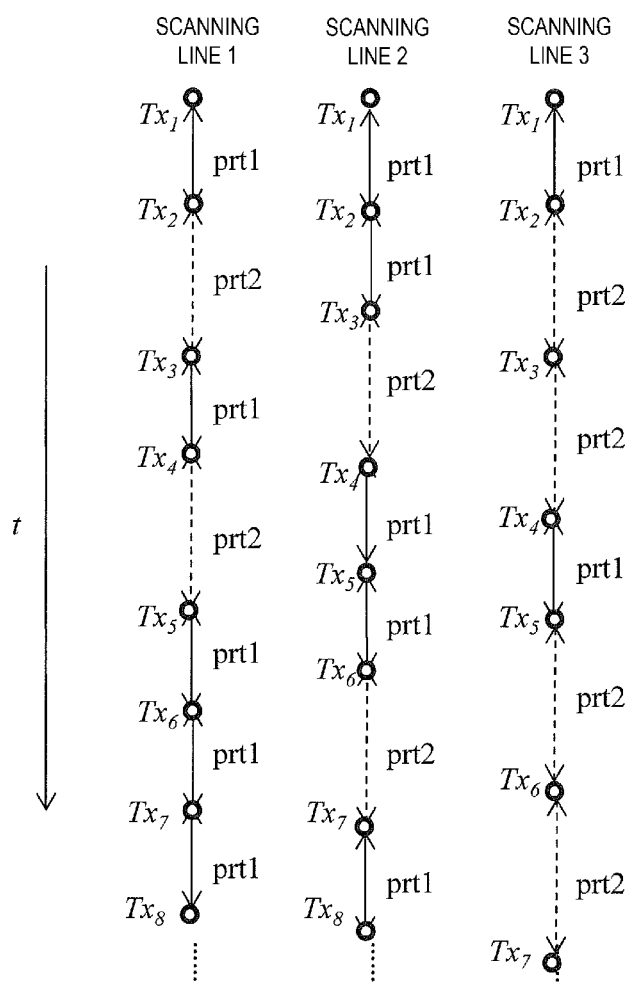

[FIG. 13]
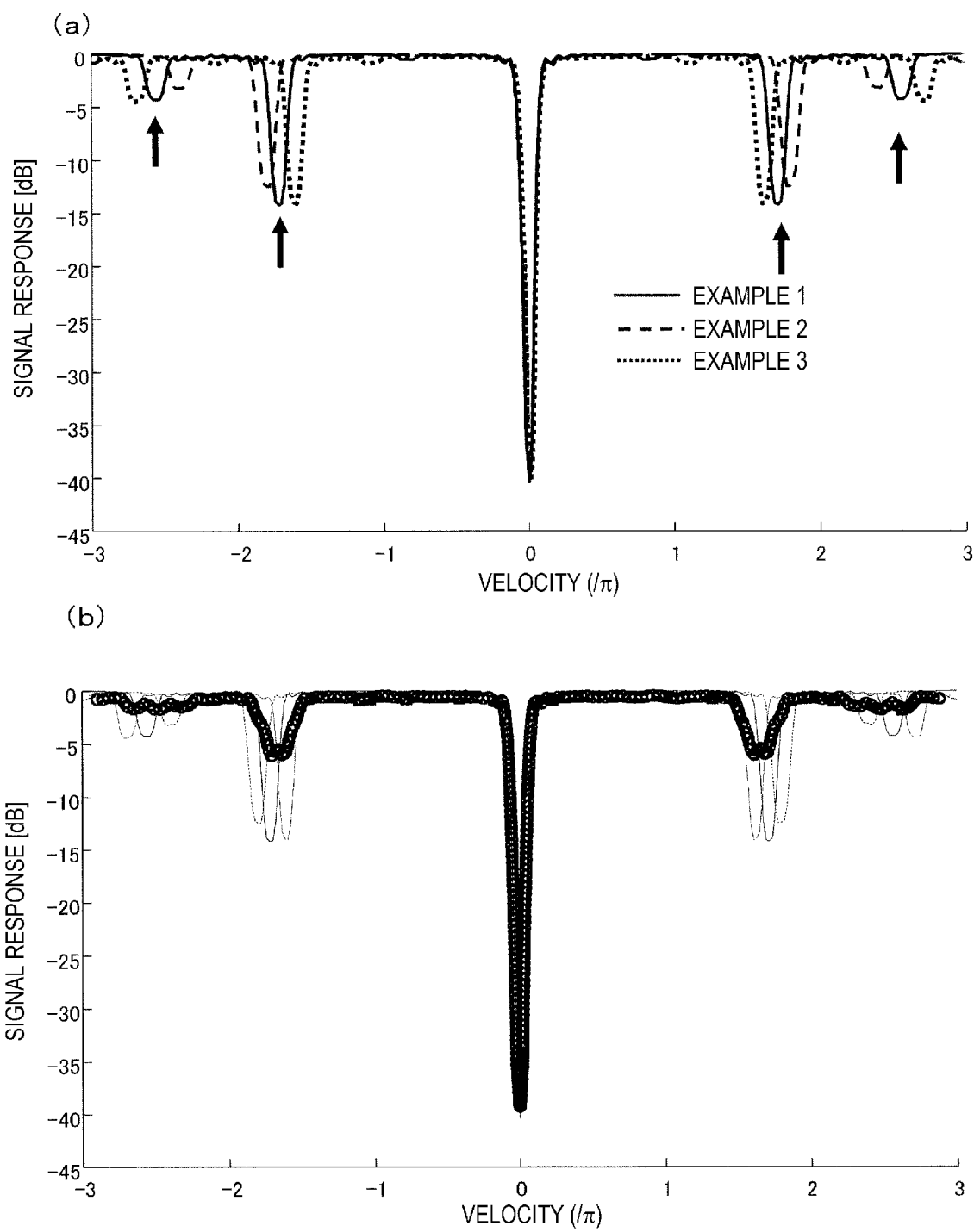

ULTRASONIC IMAGING DEVICE AND METHOD

TECHNICAL FIELD

The present invention relates to an ultrasonic imaging device that acquires blood flow information of a subject, and more particularly to a technique for acquiring blood flow velocity information in a wide dynamic range.

BACKGROUND ART

A color Doppler method is known as a technique for acquiring blood flow information in an ultrasonic imaging device. In the color Doppler method, ultrasonic waves are transmitted a plurality of times in the same direction at a predetermined repetition time (PRT: pulse repetition time), a frequency analysis is performed on a received signal received from a measurement region corresponding to the ultrasonic wave in each time, and the blood flow information is obtained. In the frequency analysis, for example, a phase difference between temporally adjacent received signals (Doppler shift amount) is obtained, and the Doppler shift amount is obtained and a blood flow velocity (Doppler velocity) is calculated by an autocorrelation calculation of the phase difference. In a calculation that acquires the blood flow information, a plurality of phase differences acquired from a data string including a plurality of received signals, which is called a packet, are averaged and used. Therefore, a frame rate of the color Doppler method depends on a packet size, and the frame rate decreases as the packet size increases.

The blood flow velocity obtained by the above color Doppler method is restricted by a repetition frequency that is a reciprocal of PRT (PRF: pulse repetition frequency). That is, a velocity higher in frequency than the PRF cannot be distinguished from a velocity lower in frequency since a phase wrap (aliasing) occurs when the phase difference is obtained. As a result, there is a problem that a dynamic range of a detectable blood flow velocity decreases.

In order to solve this problem, a method of performing times of transmission of different PRTs and using the received signals of a plurality of PRFs to expand the dynamic range of the blood flow velocity (hereafter, referred to as an unequal interval transmission method) is proposed (NPL 1, PTL 1). In this method, for example, the ultrasonic wave is transmitted in a transmission sequence in which different transmission intervals (PRT1, PRT2) are alternately combined, a received signal set of PRT1 and a received signal set of PRT2 are used to estimate a number of the phase wrapping from a relationship between a respective phase difference and a ratio of PRF, and a Doppler velocity without wrapping (referred to as a velocity without wrapping) is estimated.

CITATION LIST

Non-Patent Literature

NPL 1: IEEE TRANSACTIONS ON MEDICAL IMAGING, VOL. 35, NO. 6, pp. 1510-1521, 2016

Patent Literature

PTL 1: JP-A-2005-176997

SUMMARY OF INVENTION

Technical Problem

Since in the unequal interval transmission method in related art, it is necessary to transmit and receive at a plurality of different PRFs, compared to a case where an equal interval transmission is performed with the same packet size (hereinafter, referred to as an equal interval transmission method), at least twice the number of times of transmission and reception is required, and there is a problem that a temporal resolution of the blood flow velocity decreases, causing a large deterioration in the frame rate.

In order to prevent a decrease in the frame rate, PTL 1 adopts a method in which transmission and reception on different scanning lines are alternately performed (turbo transmission), but in this method, since it is necessary to shift a transmission interval of adjacent scanning lines in consideration of a receivable time, in order to obtain information of one scanning line, it takes at least four times as long as the equal interval transmission method in the related art. That is, a temporal resolution of a drawn blood flow velocity deteriorates to ¼.

In order to solve the above problem, an object of the invention is to provide a technique capable of preventing a deterioration of a frame rate or a temporal resolution and estimating blood flow velocity in a wide range.

Solution to Problem

In order to solve the above problem, an ultrasonic imaging device of the invention is based on the unequal interval transmission method, and calculates a blood flow velocity by using a combination of received signals in which an interval between signals (PRT) overlaps in a time direction, among a plurality of received signals obtained via a plurality of times of transmission in one transmission direction.

That is, the ultrasonic imaging device of the invention includes an ultrasonic transmitter configured to transmit an ultrasonic wave a plurality of times at different transmission intervals, an ultrasonic receiver configured to receive ultrasonic wave irradiated from the ultrasonic transmitter and reflected from a subject, and a blood flow calculator configured to process the plurality of received signals received by the ultrasonic receiver corresponding to the plurality of times of transmission and calculate blood flow information of the subject, wherein the blood flow calculator includes a data selector configured to respectively select received signal sets from ultrasonic waves having the same transmission interval for a plurality of types of transmission intervals, among the plurality of received signals, and a blood flow velocity calculator configured to calculate a blood flow velocity without wrapping using a plurality of types of received signal sets selected by the data selector, and the data selector is configured to select a temporally discontinuous received signal set as at least one of the plurality of types of received signal sets.

Advantageous Effect

By using the received signal set of at least one PRT among the plurality of types of PRTs and the temporally discontinuous received signal set, a blood flow can be calculated using a phase difference between signals of different PRTs, so that a dynamic range of the blood flow velocity that is estimable can be expanded in a manner the same as the unequal interval transmission method. By selecting the temporally discontinuous received signal set, the interval between the signals can be overlapped in the time direction at the same PRF, so that a frame rate can be shortened compared to the unequal interval transmission method in the related art. In addition, a temporal resolution of the blood flow velocity depends on a time required to acquire information for one scanning line, whereas in the invention, a received time per scanning line can be shortened compared to the method in the related art, so that the temporal resolution of the blood flow velocity can be increased compared to the unequal interval transmission method in the related art.

BRIEF DESCRIPTION OF DRAWINGS

FIG. 1 is a diagram showing an overall configuration of an embodiment of an ultrasonic imaging device of the invention.

FIG. 2A is a diagram showing a configuration and a data flow of a blood flow calculator of the ultrasonic imaging device in FIG. 1.

FIG. 2B is a diagram showing details of a Doppler processor in FIG. 2A.

FIG. 3 is a diagram showing a flow of a Doppler imaging processing by an ultrasonic imaging device according to a first embodiment.

FIGS. 4(a) and 4(b) are diagrams showing an ultrasonic transmission and reception sequence in related art, in which FIG. 4(a) shows an equal interval transmission method in the related art, and FIG. 4(b) shows an unequal interval transmission method in the related art.

FIG. 5 is a diagram showing an example of a transmission and reception sequence according to the first embodiment.

FIG. 6 is a diagram showing an embodiment of a display in the ultrasonic imaging device of the invention, in which FIG. 6(a) is a diagram showing a display in a normal mode, and FIGS. 6(b) and 6(c) are diagrams showing a display when a wrapping avoidance mode is selected.

FIG. 7 is a diagram showing a table comparing an imaging method according to the first embodiment with a method in the related art.

FIGS. 8(a) and 8(b) are diagrams showing velocity estimation simulation results of the first embodiment and the method in the related art.

FIG. 9(a) is a diagram showing a transmission and reception sequence the same as the transmission and reception sequence shown in FIG. 5, and FIGS. 9(b) and 9(c) are diagrams showing modifications thereof, respectively.

FIG. 10 is a diagram showing a configuration of a blood flow calculator according to a second embodiment.

FIG. 11 is a diagram showing an example of a transmission and reception sequence according to the second embodiment.

FIG. 12 is a diagram showing another example of the transmission and reception sequence according to the second embodiment.

FIG. 13 shows diagrams of frequency characteristics of a clutter filter, in which FIG. 13(a) is a diagram showing differences depending on the transmission and reception sequence, and FIG. 13(b) is a diagram showing the frequency characteristics when performing different control depending on the scanning line.

DESCRIPTION OF EMBODIMENTS

Embodiments of an ultrasonic imaging device and an imaging method of the invention are described.

<Embodiment of Ultrasonic Imaging Device>

In general, as shown in FIG. 1, an ultrasonic imaging device 100 includes a transmission and reception circuit 30 to which an ultrasonic probe 20 that is in contact with a subject 10 and that transmits and receives an ultrasonic wave is connected, a transmission and reception sequence controller 40 that controls transmission and reception timings or the like, a signal processor 50 that performs Doppler computation and tomographic image computation using a received signal, and a display image generator 60 that generates an image to be displayed on a display device.

The ultrasonic imaging device 100 includes an input unit 70 for a user to input numerical values and information necessary for imaging or control, and a display unit (display device) 80 that displays an image generated by the display image generator 60.

The ultrasonic probe 20 is a device in which a plurality of transducers (vibrators) are arranged in a one-dimensional direction or a two-dimensional direction, converts an electrical signal from the transmission and reception circuit 30 into an ultrasonic signal, irradiates the subject 10 with the ultrasonic signal, and detects an echo signal which is a reflected wave from the subject 10.

The transmission and reception circuit 30 includes a transmission circuit (ultrasonic transmitter) that includes an oscillator generating a signal of a predetermined frequency, and that transmits a drive signal to the ultrasonic probe by a predetermined scanning method, and a reception circuit (ultrasonic receiver) that performs a signal processing such as a phasing addition, a detection, and an amplification on the echo signal received by the ultrasonic probe. The transmission circuit may include a transmission beam former 31 that gives a separate delay time to each vibrator of the ultrasonic probe and gives directivity to an ultrasonic beam, and the reception circuit may include a reception beam former (phasing adder) 32 that gives a delay time to a signal received by each vibrator and adds the signals. A received signal output from the reception circuit after beam forming is a radio frequency (RF) signal having a frequency component depending on a blood flow velocity, and is input to the signal processor 50 as an A/D converted digital signal. An A/D converter that digitizes the RF signal may be provided in the reception circuit or may be provided in a subsequent stage of the reception circuit.

The transmission and reception sequence controller 40 controls an operation of the transmission and reception circuit 30 based on an imaging condition or a scanning condition received by the input unit 70. Examples of an imaging method include a planar imaging method for imaging a two-dimensional section and a stereoscopic imaging method for imaging a three-dimensional region, and the embodiment can adopt either one of the imaging methods. A scanning method includes a method using a continuous wave and a method using a pulse wave, and particularly in a color Doppler method, an ultrasonic transmission and reception control (Doppler transmission and reception sequence control) adopting a plurality of ultrasonic transmission and reception conditions is performed to the transmission and reception circuit 30.

In the color Doppler method, when there are a plurality of measurement modes, the transmission and reception circuit 30 and/or the signal processor 50 is controlled to operate in a set measurement mode. Examples of the measurement modes include a measurement mode in which a wrapping calculation is performed (wrapping avoidance mode) and a measurement mode in which such a calculation is not performed (normal measurement mode). For example, the measurement mode is selected by providing an operation tool 71 such as a switch or a button for selecting the wrapping avoidance mode in the input unit (including a GUI), and receiving an electric signal generated when the user operates the operation tool 71 by the transmission and reception sequence controller 40.

The signal processor 50 processes signals (digital RF signals) received by the reception circuit, and creates an ultrasonic tomographic image and calculates the blood flow velocity. For this purpose, the signal processor 50 includes a signal sorting unit 51 that sorts the RF signals into signals for creating a tomographic image and signals for calculating the blood flow velocity, a tomographic image calculator 53 that generates a tomographic image such as a B-mode image, and a blood flow calculator 55 that estimates or calculates blood flow information such as a Doppler velocity. The blood flow calculator 55 includes a data selector 553 that selects a signal set used to calculate a velocity without wrapping, and a blood flow velocity calculator 555, or the like.

FIG. 2A shows an example of the blood flow calculator 55. In an illustrated example, the blood flow calculator 55 includes a quadrature detector 551 that converts the RF signals into IQ signals each including a real part and an imaginary part, a clutter filter unit 552 that removes a signal from a stationary tissue other than a blood flow, a PRF sorting unit (data selector) 553 that sorts the IQ signals after passing through the clutter filter unit 552 depending on the PRF, Doppler processors 554 that obtain the Doppler velocity, a power, a variance, or the like using the signals sorted depending on the PRF, and a wrapping calculator 556 that calculates the velocity without wrapping using a processing result of each Doppler processor 554. In this example, the Doppler processors 554 and the wrapping calculator 556 constitute the blood flow velocity calculator 555 of FIG. 1.

As shown in FIG. 2B, each of the Doppler processors 554 further includes a velocity estimator 5541 that estimates the blood flow velocity with an autocorrelation method, a power calculator 5542, a variance estimator 5543, a post-processor 5544 that corrects an output of the velocity estimator 5541 using the power calculated by the power calculator 5542, or the like.

FIG. 2A shows a configuration in which a plurality of Doppler processors 554 are provided in parallel to a subsequent stage of the PRF sorting unit 553, but a single Doppler processor 554 can also sequentially process the signal sorted by the PRF sorting unit 553.

Some or all of functions of the above signal processor 50 may be realized by a central processing unit (CPU) of a computer reading and executing a program including an arithmetic algorithm for each function unit, or may be realized by a hardware such as an application specific integrated circuit (ASIC), a field-programmable gate array (FPGA), and a graphics processing unit (GPU).

In addition to displaying the image generated by the display image generator 60, the display unit 80 can also display a GUI or the like that functions as an input unit. The display unit 80 also displays a set imaging condition, an imaging condition set by default, information or an image serving as an imaging guide, or the like. For example, in the color Doppler, a set PRF, a measurable velocity range in the PRF, or the like may be displayed.

Next, an embodiment of Doppler imaging using the above ultrasonic imaging device is described.

First Embodiment

In this embodiment, the PRF sorting unit (data selector) 553 of the blood flow calculator 55 selects a temporally continuous received signal set and a temporally discontinuous received signal set as a plurality of types of received signal sets. Since these received signal sets have different PRFs, it is possible to calculate the velocity without wrapping by an unequal interval transmission method using a plurality of types of PRFs.

Hereinafter, this embodiment will be described with reference to FIG. 3.

When the Doppler imaging is started and the user operates a wrapping avoidance mode button 71 of the input unit 70 (S301), in response to the operation, the transmission and reception sequence controller 40 starts switching (S302) a transmission and reception sequence to an unequal interval transmission combining a plurality of preset PRTs (S303). Accordingly, an ultrasonic transmission at an unequal interval by the transmission beam former 31 and the ultrasonic probe 20 and a reception by the reception beam former 32 are started.

As shown in FIG. 4, the transmission and reception sequence sets timings of transmitting a transmission pulse and timings of receiving a received signal that is a reflected wave generated from a predetermined depth (measurement region) by the transmission pulse for the same transmission direction, where Tx1, Tx2 . . . are times required for the transmission, and Rx1, Rx2 . . . are times required for the reception. The times required for the transmission (Tx1, Tx2 . . . ) are determined by a wavelength of a transmission waveform and are constant. The times required for the reception (Rx1, Rx2 . . . ) are determined by a data reception depth and are constant. A data string including received signals obtained from the predetermined depth by a plurality of times of transmission is called a packet. PRT is an interval between Tx(i−1) and Tx(i) (i is an integer of 2 or more), and in a case of an equal interval transmission, the transmission is repeated with a single PRT, as shown in FIG. 4(a). In a case of an unequal interval transmission, a plurality of types of PRTs, for example, prt1 and prt2 (prt1≠prt2) are alternately repeated, as shown in FIG. 4(b). Here, prf1 and prfi which are reciprocals of prt1 and prti satisfy a relationship of Equation (1).

[Equation1]

$$prfi = \{p(i)/q(i)\} \times prf1 \quad (1)$$

In the equation, p (i) and q (i) are integers that are not divisible by each other, and differ depending on "i".

FIG. 4(b) shows a case where there are two types of PRTs, but there may be more types of PRTs.

In the transmission and reception sequence of the unequal interval according to this embodiment, for example, when two types of PRTs (prt1, prt2) are used, as shown in FIG. 5, the transmission is performed such that prt1 and prt2 are repeated alternately with an interval between a first transmission pulse Tx1 and a second transmission pulse Tx2 being prt1, and an interval between the second transmission pulse Tx2 and a third transmission pulse Tx3 being prt2. This is the same as the unequal interval transmission shown in FIG. 4(b), but after or during the alternate transmission of prt1 and prt2, only one of prt1 and prt2 is repeated, and finally, the number of received signals of prt1 or prt2 and the number of received signals of "prt1+prt2" and "prt2+prt1" are made to be the same. Here, "prt1+prt2" and "prt2+prt1" refer to received signal sets whose transmission intervals of two transmission pulses are a sum of prt1 and prt2 (prt3=prt1+prt2). In an example shown in FIG. 5, prt3 is a pulse interval in which n of Txn is an odd number, such as an interval between Tx1 and Tx3 and an interval between Tx3 and Tx5, and a pulse interval in which n of Txn is an even number, such as an interval between Tx2 and Tx4 and an interval between Tx4 and Tx6. In the example shown in FIG. 5, a combination of every other timing is illustrated as the temporally discontinuous received signal set, but a combination having an interval of two or more received signals is acceptable as well.

By performing transmission and reception in this way, a plurality of received signal sets of each of a plurality of types of PRFs are obtained corresponding to a plurality of types of transmission intervals.

Next, the blood flow calculator 55 performs a Doppler signal processing on the received signals received from the reception circuit 32 (S304). Specifically, as shown in FIG. 2A, first, the quadrature detector 551 converts the received signals (RF signals) into ultrasonic complex signals (IQ signal) each including a real part and an imaginary part, and the clutter filter unit 552 removes a low frequency component corresponding to signals from a stationary part. Next, the PRF sorting unit 553 sorts IQ signal sets depending on the PRT. In an example shown in FIG. 2A, the PRF sorting unit 553 sorts the IQ signal sets (prt1, prt2, and prt3) depending on the three pulse repetition frequencies corresponding to prt1, prt2, and prt3, respectively. Here, prt1 and prt2 correspond to received signal sets adjacent to each other and follow a temporal order, as shown in FIG. 5, whereas prt3 is the interval between Tx1 and Tx3 or the interval between Tx2 and Tx4, and the intervals partially overlap each other. The PRF sorting unit 553 performs the above data sorting (selection) based on a data number assigned to a piece of data received in each reception Rx(n).

The Doppler processors 554 calculate the Doppler velocity, the power, and the variance using the data sorted depending on the PRF. For example, in a case of prf1 and prf2, the velocity estimator 5541 uses two temporally continuous received signals (IQ signals), calculates a Doppler shift based on a phase difference between the two signals, and estimates a velocity from a Doppler transition (S304-1). Since a plurality of received signal sets having the same PRF are obtained, the phase difference can be calculated by a known method such as the autocorrelation method or an improved method thereof using a plurality of phase differences. The power calculator 5542 and the variance estimator 5543 calculate a signal intensity (power) and the variance for each sample in the measurement region. A velocity Vel, a signal power Pow, and a variance Var at a certain point x can be calculated by the following Equations (2) to (4).

[Equation 2]
$$Vel^x = \sum_N E_N^x * \overline{E_{N-1}^x} \quad (2)$$

[Equation 3]
$$Pow^x = \sum_N E_N^x * \overline{E_N^x} \quad (3)$$

[Equation 4]
$$Var^x = 1 - \frac{\left|\sum_N E_N^x * \overline{E_{N-1}^x}\right|}{Pow^x} \quad (4)$$

In the equations, E is an IQ signal after a quadrature detection, and N is the number of data sets (the same hereinafter).

In step S304-1, the blood flow information may be calculated for both of, or for only one of prf1 and prf2.

In a case of prf3, the Doppler processors 554 similarly calculate the blood flow information using the two received signals that are prf3 (S304-2). In the example shown in FIG. 5, while prt1 and prt2 are alternately repeated (from Tx1 to Tx+1), the phase difference is obtained and the Doppler velocity or the like is estimated using a set of an odd-numbered received signal and a next odd-numbered received signal and a set of an even-numbered received signal and a next even-numbered received signal. For example, the post-processor 5544 determines a validity of a result estimated by the velocity estimator 5541 based on the variance estimated by the variance estimator 5543, and performs correction or the like as necessary.

Next, the wrapping calculator 556 performs calculation for obtaining the velocity without wrapping (S305). To calculate the velocity without wrapping, the blood flow information calculated in step S304-1 by the blood flow calculator 55 (the blood flow velocity calculated from prf1 or prf2) and the blood flow information calculated in step S304-2 (the blood flow velocity calculated from prf3) are used. Here, a case where a blood flow velocity v1 of prf1 and a blood flow velocity v3 of prf3 are used is described as an example.

In general, a measurement limit velocity (Nyquist velocity) $V_N$ in a Doppler measurement is expressed by the following Equation (5).

[Equation 5]
$$v_N = \frac{prf \times c}{4 \times f_0} \quad (5)$$

In the equation, "prf" is the pulse repetition frequency, c is a velocity of sound, and $f_0$ is a center frequency of the ultrasonic wave.

When the velocity to be measured exceeds the Nyquist velocity, the Doppler velocity $V_D$ that is actually obtained by wrapping (measurement Doppler velocity) is expressed by Equation (6).

[Equation6]
$$V_D = V_A - 2n \cdot V_N \quad (6)$$

In the equation, $V_A$ is the Doppler velocity when wrapping is absent (Doppler velocity without wrapping), and n is the number of wrapping times.

The Nyquist velocity expressed by Equation (7) varies depending on the pulse repetition frequency prf, for example, when there is a relationship (prf3={p/q}×prf1) shown in Equation (1) between prf1 and prf3, the Nyquist velocity also has a similar relationship as shown in Equation (7).

[Equation7]
$$V_{N3} = \{p/q\} \times V_{N1} \quad (7)$$

From Equations (5) to (7), the following relationship is established.

[Equation8]
$$q \cdot \{(V_{N3} - V_{N1})/2V_{N1}\} = n_{N1}q - n_{N3}p \quad (8)$$

By solving Equation (8) using the following constraint conditions (Equation (9) and Equation (10)), the numbers of wrapping $n_{N1}$ and $n_{N3}$ are obtained.

[Equation9]

$$|n_{N1}q - n_{N3}p| \leq (1/2) \times (p+q) \quad (9)$$

[Equation10]

$$|n_{N3}| \leq \text{ceiling}\{(q-1)/2\} \quad (10)$$

By applying the numbers of wrapping $n_{N1}$ and $n_{N3}$ obtained in this way to Equation (6), the velocity without wrapping is obtained by Equation (6) at each prf. An average value of the velocity without wrapping obtained at each prf is taken as a Doppler velocity without wrapping $V_A$ to be measured.

In the above description, a case where data of prf1 and prf3 are used as different types of PRFs for the Doppler calculation is described, but prf2 and prf3 may be combined, or all data of prf1 to prf3 may be used. In the former case, after prt1 and prt2 are alternately performed in a sequence of FIG. 5, only prt2 is repeated so that the number of packets of prt3 and the number of packets of prt2 are the same. In the latter case, the transmission and reception may be performed in a sequence the same as the unequal interval transmission method in the related art shown in FIG. 4(b). In this case, a frame rate is similar as in a method in the related art, but an accuracy of estimating the velocity without wrapping is improved.

The display image generator 60 creates a display image using the blood flow information estimated or calculated by the Doppler processors 554, and displays the display image on the display unit 80 (S306). A display form of the blood flow information is not particularly limited, but in a general color Doppler method, as shown in FIG. 6(a), a flow velocity change in a Doppler measurement region is displayed in color on a B-mode image 81 created by the tomographic image calculator 53, a width of a measurable flow velocity, that is, a dynamic range of the flow velocity is displayed by a color bar, a gradation bar or the like 82, and the PRF is numerically displayed in a PRF display box 83. Further, a mode display box 84 that displays the measurement mode or the like may be provided.

In this embodiment in which the velocity without wrapping is calculated using the plurality of types of PRFs, the dynamic range of the flow velocity is enlarged as compared with a measurement in a mode in which the wrapping is not avoided (normal measurement mode). Therefore, in accordance with the enlargement, for example, as shown in FIG. 6(b), a length of the color bar or gradation bar 82 (FIG. 6(a)) displayed in the normal measurement mode may be changed, or as shown in FIG. 6(c), the length of the color bar or gradation bar 82 may be left as it is, and a gradation width thereof may be changed.

Since a PRF value during measurement in the wrapping avoidance mode is also different from that of the normal measurement mode, the PRF value displayed in the box 83 is changed also during the measurement in the wrapping avoidance mode. In the wrapping avoidance mode in the related art, the plurality of types of PRFs set during the measurement are displayed, but in this embodiment, PRF values sorted by the PRF sorting unit 553 (a plurality of values) are displayed.

According to the ultrasonic imaging device according to this embodiment, by using the temporally discontinuous received signal set as at least one of the plurality of types of received signal sets used for the blood flow velocity estimation, the frame rate for acquiring the blood flow velocity can be improved.

Assuming 9-packet transmission, FIG. 7 shows a result of comparing a time to acquire one scanning line (flow velocity resolution), a velocity range and a frame rate according to this embodiment with those of the methods in the related art (the equal interval transmission method and the unequal interval transmission method). In such calculation, assuming that the velocity range is three times the Nyquist velocity, PRT2=PRT1×(4/3). In order to make SN equal, each average number of addition of phase differences of PRT1 and PRT3 in the method according to this embodiment is ensured to be the same as in the method in the related art.

As shown in FIG. 7, in the unequal interval transmission method in the related art, the frame rate decreases to 0.4 times compared to the equal interval transmission method, but in the method according to this embodiment, the number is 0.7 times and is an improvement of about 1.8 times compared to the unequal interval transmission method in the related art.

FIG. 8 shows a simulation result of a velocity distribution of the velocity without wrapping obtained by the unequal interval transmission method in the related art and a velocity distribution of the velocity without wrapping obtained by the method according to this embodiment. FIG. 8(a) shows a result of the method according to this embodiment, and FIG. 8(b) shows a result of the unequal interval transmission method in the related art. Simulation conditions are as follows.

Scanning type: sector
Center frequency ($f_o$): 3 MHz
PRF: prf1=10 kHz, prf2=7.5 kHz, prf3=6.8 kHz
Total number of packets (N): 15
Maximum blood flow velocity: 1 m/s As can be seen from FIGS. 8(a) and 8(b), according to this embodiment, a velocity estimation result almost equivalent to the unequal interval transmission method in the related art can be obtained.

Modification of First Embodiment

In the transmission and reception sequence according to the first embodiment shown in FIG. 5, after repeating two types of PRTs alternately, only one PRT is repeated, but the transmission and reception sequence is not limited thereto, and a plurality of types of PRTs may be arranged with a certain regularity. Modifications of the transmission and reception sequence are shown in FIGS. 9(b) and 9(c). FIG. 9(a) shows the transmission and reception sequence of FIG. 5 together. In FIG. 9, the reception timings are omitted.

An example of FIG. 9(b) repeats a plurality of times of transmission in a unit of PRT1-PRT2-PRT1, and uses a received signal set of PRT1 and a signal set of PRT3 (PRT1+PRT2) to calculate the blood flow velocity. An example of FIG. 9(c) repeats a plurality of times of transmission in a unit of PRT1-PRT2-PRT2, and uses a received signal set of PRT2 and the signal set of PRT3 (PRT1+PRT2) to calculate the blood flow velocity.

Similar as the transmission and reception sequence in FIG. 9(a), in a case where transmission and reception sequences of these modifications are adopted, the frame rate is also improved as compared with the equal interval transmission method in the related art with the same packet size. For the time to acquire the one scanning line, the transmission and reception sequence in FIG. 9(b) is the same as the transmission and reception sequence in FIG. 9(a). In a case of PRT1<PRT2, the transmission and reception sequence in FIG. 9(c) takes a longer time to acquire one scanning line than those in FIGS. 9(a) and 9(b), but the time can be shorten compared with the equal interval transmission method in the related art.

Second Embodiment

An ultrasonic imaging device according to this embodiment is characterized in that the transmission and reception sequence is independently controlled for each scanning line. That is, in the ultrasonic imaging device according to this embodiment, the transmission and reception sequence controller independently controls transmission intervals of ultrasonic waves in the plurality of times of transmission for each of the ultrasonic waves in a plurality of transmission directions. The blood flow calculator includes an averaging unit that averages the blood flow information calculated using received signals respectively obtained from the ultrasonic waves in adjacent transmission directions.

A configuration example centering on the signal processor of the ultrasonic imaging device according to this embodiment is shown in FIG. 10. In FIG. 10, elements having functions the same as those shown in FIGS. 1 and 2A are denoted by the same reference numerals, and a redundant description is omitted. As shown in FIG. 10, the blood flow calculators 55 according to this embodiment are configured to calculate the blood flow information (blood flow velocity, dispersion, power, or the like) for each scanning line, and includes an averaging unit 57 that averages the blood flow information of each scanning line. In FIG. 10, the averaging unit 57 is illustrated in a subsequent stage of the blood flow calculators 55, but it is also possible to average intermediate values among values calculated by the blood flow calculators 55, and a position of the averaging unit 57 is not related to a flow of processing. Although a plurality of blood flow calculators 55 are shown, it is also possible to perform the processing with a single blood flow calculator.

In this embodiment, a procedure for the Doppler imaging is substantially the same as in the first embodiment, but in this embodiment, when the transmission and reception sequence controller 40 performs control so as to perform the transmission and reception a plurality of times at the plurality of types of transmission intervals, the transmission and reception timings are different for each of the plurality of transmission directions (scanning lines) in which the ultrasonic probe performs transmission. However, the numbers of packets on the scanning line are the same.

Examples of different transmission and reception sequences for each scanning line are shown in FIGS. 11 and 12. In FIGS. 11 and 12, a vertical direction is a time axis direction. In the example shown in FIG. 11, control is performed so that the transmission and reception sequences are different alternately in odd-numbered scanning lines and in even-numbered scanning lines. In the odd-numbered scanning lines, for example, transmission of prt1 and transmission of prt2 are performed alternately first and transmission of prt1 is repeated in a second half, and in the even-numbered scanning lines, prt1 is repeated a predetermined number of times first, and the transmission of prt1 and the transmission of prt2 are alternately performed in the second half. In either case, the number of packets is the same, and the number of prt1 and the number of prt3 (prt1+prt2) are set to the same number. In the example shown in FIG. 12, different control is performed on three spatially continuous scanning lines. For example, in the first embodiment, three examples of the transmission and reception sequences are shown in FIGS. 9(a) to 9(c), and these three different transmission and reception sequences are applied to scanning lines 1 to 3. Although an order of the three transmission and reception sequences is not limited, in each case, the number of packets is the same, and the number of prt1 and the number of prt3 (prt1+prt2) are set to the same number.

The blood flow calculator 55 processes received signals of each scanning line, and calculates and estimates the Doppler measurement velocity (including wrapping) $V_D$, the velocity without wrapping $V_A$, the number of times of wrapping n, or the like for each scanning line. The averaging unit 57 averages the values calculated or estimated by the blood flow calculator 55 for each scanning line between adjacent scanning lines.

For example, in a case of the transmission and reception sequence shown in FIG. 11, $V_{Dave}=(V_{D1}+V_{D2})/2$ may be calculated from the Doppler measurement velocities calculated for the scanning line 1 and the scanning line 2, and the velocity without wrapping may be estimated using the averaged Doppler measurement velocity. Alternatively, the numbers of wrapping $n_{N1}$ and $n_{N3}$ estimated for each PRF Nyquist frequency in each scanning line may be averaged, and a averaged number of wrapping $n_{Nave}$ may be used to estimate the velocity without wrapping $V_A$. In a case of the transmission and reception sequences shown in FIG. 12, values calculated for the three scanning lines are averaged.

As described above, according to this embodiment, it is possible to improve an estimation accuracy of the velocity without wrapping by making the transmission and reception sequences different for each scanning line and averaging values obtained for each scanning line.

According to this embodiment, it is possible to reduce a sensitivity reduction region where a signal is blocked in signals after applying a clutter filter 52 even in a region other than a desired low frequency region. This effect is described using a graph showing frequency characteristics of the clutter filter 52. FIG. 13(a) is a graph conceptually illustrating the frequency characteristics of the clutter filter 52, where a horizontal axis indicates a measurement velocity (corresponding to a frequency), and a vertical axis indicates a signal response, that is, a sensitivity (dB). The clutter filter has a characteristic of blocking a signal from the stationary tissue, that is, a frequency of zero velocity, but a blind frequency having a frequency determined by a sum of the two PRTs (prt1, prt2) (f=1/(prt1+prt2)) as a period is generated (indicated in FIG. 13(a) by arrows). The frequency characteristics are affected by the transmission and reception sequences. For example, the transmission and reception sequence in FIG. 9(a) has the frequency characteristics are indicated by solid lines in the drawing, whereas the transmission and reception sequences in FIGS. 9(b) and 9 (c) have the frequency characteristics indicated by broken lines and dotted lines, respectively.

In this embodiment, by making the transmission and reception sequences different for each scanning line, the frequency characteristics become an average value thereof, and thus it is possible to prevent a sensitivity reduction in the sensitivity reduction region. For example, as shown in FIG. 12, in the case of the transmission and reception sequences in which the transmission and reception sequences of the three scanning lines are made different, three frequency characteristics shown in FIG. 13(a) are averaged, resulting in a graph as shown by a thick line in FIG. 13(b). From this graph, it can be seen that sensitivity reductions in three sensitivity reduction regions indicated by arrows in FIG. 13(a) are averaged and the sensitivity reductions are prevented.

As above, although each embodiment of the ultrasonic imaging device of the invention is described, a device configuration, a transmission and reception sequence or the like described in each embodiment are examples, some elements can be appropriately deleted or changed, and it is also included in the invention to add other elements not described.

REFERENCE SIGN LIST 10 subject
20 ultrasonic probe
30 transmission and reception circuit
31 transmission circuit
32 reception circuit
40 transmission and reception sequence controller
50 signal processor
51 signal sorting unit
53 tomographic image calculator
55 blood flow calculator
551 quadrature detector
552 clutter filter unit
553 PRF sorting unit (data selector)
554 Doppler processor (blood flow velocity calculator)
5541 velocity estimator
5542 power calculator
5543 variance estimator
5544 post-processor
555 blood flow velocity calculator
556 wrapping calculator (blood flow velocity calculator)
57 averaging unit
60 display image generator
70 input unit
80 display unit

The invention claimed is:

1. An ultrasonic imaging device, comprising:
an ultrasonic transmitter configured to transmit ultrasonic waves a plurality of times at different transmission intervals;
an ultrasonic receiver configured to receive ultrasonic waves irradiated from the ultrasonic transmitter and reflected from a subject; and
a blood flow calculator configured to process a plurality of received signals received by the ultrasonic receiver corresponding to the plurality of times of transmission and calculate blood flow information of the subject, wherein
the blood flow calculator includes a data selector configured to respectively select received signal sets from ultrasonic waves having the same transmission interval for a plurality of types of transmission intervals, among the plurality of received signals, and a blood flow velocity calculator configured to calculate a blood flow velocity without wrapping using a plurality of types of received signal sets selected by the data selector, and
the data selector is configured to select a temporally discontinuous received signal set as at least one of the plurality of types of received signal sets.

2. The ultrasonic imaging device according to claim 1, wherein
the blood flow velocity calculator is configured to calculate the blood flow velocity without wrapping using a temporally continuous received signal set having the same transmission interval and a temporally discontinuous received signal set.

3. The ultrasonic imaging device according to claim 1, further comprising:
a transmission and reception sequence controller configured to control transmission and reception timings of the ultrasonic waves, wherein
the transmission and reception sequence controller is configured to control the plurality of types of transmission intervals such that in the plurality of times of transmission, a number of the temporally continuous received signal set and a number of the temporally discontinuous received signal set are the same.

4. The ultrasonic imaging device according to claim 1, further comprising:
a transmission and reception sequence controller configured to control transmission and reception timings of the ultrasonic wave, wherein
the transmission and reception sequence controller is configured to arrange the plurality of types of transmission intervals according to a predetermined rule in the plurality of times of transmission.

5. The ultrasonic imaging device according to claim 1, further comprising:
a transmission and reception sequence controller configured to control transmission and reception timings of the ultrasonic wave, wherein
the transmission and reception sequence controller is configured to, for ultrasonic waves in each of a plurality of scanning directions, independently control transmission intervals of the ultrasonic waves in the plurality of times of transmission.

6. The ultrasonic imaging device according to claim 5, wherein
ultrasonic waves in adjacent scanning directions among the plurality of scanning directions have the same combination of the plurality of types of transmission intervals and different transmission timings.

7. The ultrasonic imaging device according to claim 5, wherein
the blood flow calculator further includes an averaging unit configured to average the blood flow information calculated using received signals respectively obtained from ultrasonic waves in adjacent scanning directions.

8. The ultrasonic imaging device according to claim 1, further comprising:
a display image generator configured to cause a display device to display the blood flow information calculated by the blood flow calculator and a measurable velocity range, wherein
the display image generator is configured to change a display of the velocity range to be displayed by the display device according to the transmission interval of the received signal set used by the blood flow velocity calculator to calculate the blood flow velocity.

9. The ultrasonic imaging device according to claim 8, wherein
the display image generator is configured to display the velocity range with a gradation bar, and change a length of the gradation bar or a degree of a gradation change according to the transmission interval used for calculating the blood flow velocity.

* * * * *